(12) United States Patent
Laugier et al.

(10) Patent No.: US 8,236,781 B2
(45) Date of Patent: Aug. 7, 2012

(54) HYDROGEL OF CHITOSAN CARBOXYALKYLAMIDE, PREPARATION THEREOF AND COSMETIC AND DERMATOLOGICAL USE THEREOF

(76) Inventors: Elisabeth Laugier, Geneve (CH); Franck Gouchet, Marcilly En Gault (FR); Jean-Pierre Perraud, Paris (FR)

( * ) Notice: Subject to any disclaimer, the term of this patent is extended or adjusted under 35 U.S.C. 154(b) by 403 days.

(21) Appl. No.: 12/668,047

(22) PCT Filed: Jul. 1, 2008

(86) PCT No.: PCT/FR2008/051214
§ 371 (c)(1),
(2), (4) Date: Jan. 7, 2010

(87) PCT Pub. No.: WO2009/007635
PCT Pub. Date: Jan. 15, 2009

(65) Prior Publication Data
US 2010/0183724 A1    Jul. 22, 2010

(30) Foreign Application Priority Data
Jul. 12, 2007 (FR) ..................... 07 05049

(51) Int. Cl.
*A61K 31/722* (2006.01)
*A61K 8/02* (2006.01)
(52) U.S. Cl. .......................... 514/55; 424/401
(58) Field of Classification Search ......... 514/55; 424/401
See application file for complete search history.

(56) References Cited

U.S. PATENT DOCUMENTS

| 6,124,273 | A | 9/2000 | Drohan et al. |
| 2005/0113773 | A1 | 5/2005 | Yoshii et al. |

FOREIGN PATENT DOCUMENTS

| FR | 2 736 835 | 1/1997 |
| WO | WO 03/068281 | 8/2003 |

OTHER PUBLICATIONS

International Preliminary Report on Patentability dated Feb. 16, 2010 for Application No. PCT/FR2008/051214.
Boucard, N. et al., "The use of physical hydrogels of chitosan for skin regeneration following third-degree burns," Biomaterials, vol. 28 (24) (Aug. 2007) pp. 3478-3488.
International Search Report dated Mar. 12, 2008 for Application No. PCT/FR2008/051214.
Kiyozumi, T. et al., "The effect of chitosan hydrogel containing DMEM/F12 medium on full-thickness skin defects after deep dermal burn," Burns: Journal of the International Society for Burn Injuries, vol. 33(5) (Aug. 2007) pp. 642-648.
Suh, J.K. et al., "Application of chitosan-based polysaccharide biomaterials in cartilage tissue engineering: a review," Biomaterials, vol. 21(24) (Dec. 2000) pp. 2589-2598.

*Primary Examiner* — Gina C Yu
(74) *Attorney, Agent, or Firm* — Frost Brown Todd LLC

(57) ABSTRACT

The present invention relates to a hydrogel of chitosan carboxyalkylamide, characterised in that it has a pH value close to that of the skin, comprised between 6.5 and 7.2, and in that the chitosan carboxy-alkylamide is constituted by 40 to 90 mole % of D-glucosamine N-carboxyalkylamide units of formula (I)

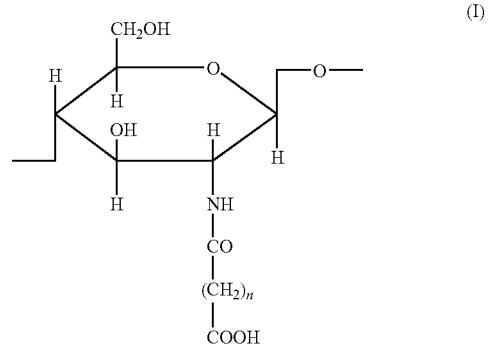

where n represents an integer ranging from 1 to 8, from 60 to 10 mole % of protonated D-glucosamine units, and from 5 to 15 mole % of N-acetyl-D-glucosamine units.
The present invention also relates to a dehydration product of such a gel and the cosmetic and/or dermatological utilisation of the gel and the dehydration product.

16 Claims, 1 Drawing Sheet

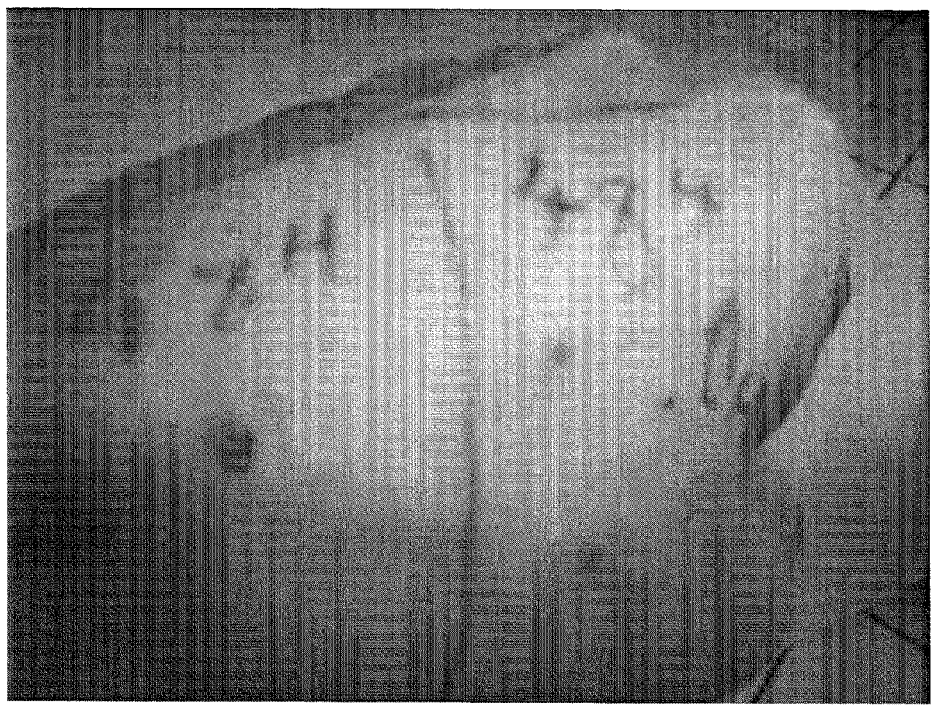

HYDROGEL OF CHITOSAN CARBOXYALKYLAMIDE, PREPARATION THEREOF AND COSMETIC AND DERMATOLOGICAL USE THEREOF

The present invention relates to a thixotropic hydrogel of chitosan carboxyalkylamide intended for the cosmetic and dermatological treatment of skin burns.

Along with cellulose, chitin is one of the most widespread natural polymers. It is for example obtained from the exoskeleton of certain crustaceans and insects. Chitin is made up of N-acetylglucosamine units linked together by 1,4-beta linkages. Chitosan is the product of deacetylation of chitin by hydrolysis, this hydrolysis converting at least some of the N-acetyl-glucosamine units to glucosamine units. It is generally agreed that chitin exhibiting a deacetylation level greater than 50% be designated by the term "chitosan". The deacetylation of chitin generally increases the solubility of the polymer in water, but this solubilisation then becomes dependent on the pH, in other words chitosan exhibiting a high level of deacetylation is only soluble in an acid medium, generally at a pH lower than 6, when a sufficient proportion of its amine groups are protonated.

The excellent biocompatibility of both of these polymers and the biodegradability of chitin and to a lesser extent of chitosan have long been known. In addition, the bacteriostatic and fungistatic properties of these polymers have been described. Moreover, their capacity to activate the healing of chronic or acute skin lesions, whether superficial (epidermal) or deep, i.e. affecting the dermis, has been demonstrated.

Thus, the French patent application FR 2 736 835 discloses a dressing for chronic wounds based on chitin with a deacetylation level of 40% at most. This dressing takes the form of a relatively rigid, transparent hydrogel.

International patent application WO 03/068281 discloses a dressing, not based on chitin, but based on chitosan having a deacetylation level of at least 60%, preferably comprised between 94 and 98%. This dressing also takes the form of a patch of thickness between 1 and 10 mm, optionally immobilised on a support, having mechanical properties sufficient for it to be capable of being handled and placed on the wound to be protected and treated.

Finally, U.S. Pat. No. 6,124,273 discloses a hydrogel based on cross-linked chitin containing an active ingredient, in particular a protein, intended to be released into the wound.

The purpose of the present invention is to exploit the known healing properties of chitosan not in the form of a dressing based on a relatively rigid hydrogel such as is described in the above documents of the prior art, but in the form of a product which is easier to use, and capable of being applied easily, as a cream or an ointment, if necessary on relatively wide areas of the skin. Such utilisation would enable the use of chitosan not only as a dressing for medical use, but also for the cosmetic treatment of light, superficial burns, due for example to prolonged exposure to the sun.

The Applicant therefore set itself the objective of perfecting a thixotropic hydrogel of chitosan, i.e. a physical gel (as opposed to a chemical gel with points cross-linked by covalent bonding) which, at rest, has the consistency of a gel, but which, when it is subjected to shear forces, has a viscosity low enough for it to be capable of being spread easily on large areas of the skin. This hydrogel should have a pH relatively close to that of the skin, preferably comprised between 6.5 and 7.2. In fact, though pH values outside this range are entirely compatible with application onto healthy skin, the Applicant has found that rapid and effective relief of the pain caused by burns, whether superficial or deep, was only obtained at the price of adjustment of the pH of the product to a range close to that of the skin.

The Applicant then encountered the problem of the insufficient solubility of weakly acetylated chitosan in this pH range. In fact, during the neutralisation of an acidic solution of chitosan, a precipitate forms at a pH of about 5 to 6 and the preparation of a thixotropic hydrogel proves to be impossible.

The present invention is based on the discovery that it was possible to prepare a thixotropic hydrogel, having the consistency of a cream or ointment, and having a pH close to that of the skin (pH=6.9) by converting at least 40%, preferably at least 50%, of the amine functions of the glucosamine units of a chitosan having a deacetylation level of at least 85%, to COOH functions by reacting them with an anhydride of an appropriate carboxylic diacid.

Consequently, the subject of the present invention is a thixotropic hydrogel of chitosan carboxyalkylamide, characterised in that it has a pH value close to that of the skin, comprised between 6.5 and 7.2, preferably between 6.8 and 7.0, and in that the said chitosan carboxyalkylamide is constituted by from 40 to 90 mole %, preferably from 50 to 80 mole %, and in particular from 50 to 75 mole %, relative to the total number of (A) and (B) units, of D-glucosamine N-carboxyalkylamide units of formula (I) ((A) units)

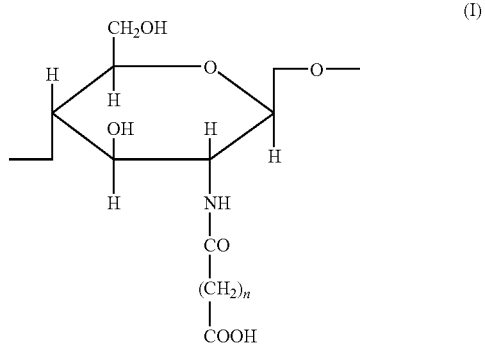

where n represents an integer ranging from 1 to 8, preferably from 1 to 4, and in particular equal to 2, or a physiologically acceptable base addition salt thereof, from 60 to 10 mole %, preferably from 50 to 20 mole %, in particular from 50 to 25 mole %, relative to the total number of (A) and (B) units, of protonated D-glucosamine units of formula (II) ((B) units)

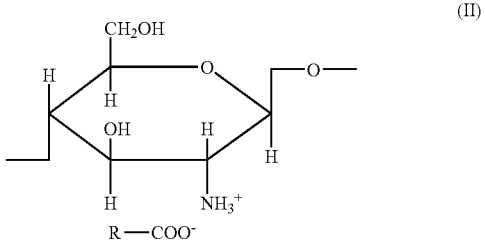

wherein R represents a $C_{1-4}$ alkyl residue, and from 5 to 15 mole %, relative to the total number of (A), (B) and (C) units, of N-acetyl-D-glucosamine units ((C) units).

As indicated above, such a hydrogel must be thixotropic, i.e. has a viscosity which in the absence of shear forces tends to infinity, i.e. the gel flows very slowly or not at all. When it is subjected to shear forces, for example during spreading onto the skin, its viscosity decreases. The Brookfield viscosity of the thixotropic gel of the present invention, measured with a Brookfield viscosimeter (needle No. 4, 30-60 r.p.m., 20° C.) is preferably comprised between 200 and 8000 centipoises, in particular between 300 and 1000 centipoises.

The chitosan forming the hydrogel of the present invention is thus an acid addition salt of a product of the acetylation of chitosan with an anhydride of a $C_{3-10}$ carboxylic diacid. The acid used to acidify the amine functions of the chitosan not having reacted with the anhydride is an organic acid of formula RCOOH where R represents a $C_{1-4}$ alkyl group. Preferably, the organic acid used for this acidification is acetic acid, i.e. R represents a methyl group. This acid is generally used during the dissolution of the chitosan in water before the reaction with the acid anhydride and the neutralisation of the chitosan carboxyalkylamide obtained as reaction product.

In order to obtain a hydrogel of appropriate consistency, the concentration of the chitosan carboxyalkylamide is preferably comprised between 0.5 and 3% by weight, in particular between 1 and 2% by weight. A concentration less than 0.5% will generally give a gel of too low a viscosity which runs off, even in the absence of shear forces, whereas a concentration beyond 3% by weight results in excessively rigid gels of the type of those described in FR 2 736 835 and WO 03/068281, which do not lend themselves to easy spreading on large areas of the skin.

The appropriate contents of chitosan carboxyalkyl-amide indicated above of course depend on the average molecular mass of the chitosan derivatives used. The greater the molecular mass of the polymer, the smaller is the concentration necessary to obtain an appropriate consistency.

The chitosan carboxyalkylamides forming the hydrogel of the present invention generally have a weight-average molecular mass comprised between 10 000 and 800 000 Dalton, preferably between 50 000 and 200 000 Dalton.

This molecular mass can be reduced, during the preparation of the hydrogel, by treating the aqueous suspension or the acid solution of chitosan with hydrogen peroxide.

The hydrogel of the present invention preferably contains, in addition to water, a texturizing agent selected from the polyols, intended to ensure good spreading of the gel on the skin. The hydrogel of the present invention preferably contains from 0.1 to 40% by weight, in particular from 0.1 to 20% by weight, of at least one polyol. The preferred polyol is glycerol.

The hydrogel of chitosan carboxylamide of the present invention has an immediate pain-soothing effect, probably due to the moisturising and cooling effect, and to the absence of any irritant qualities due to acidic or basic pH. This pain-soothing action can be reinforced and/or prolonged in a synergistic manner by the incorporation of an extract of *Calendula officinalis*, well known for its healing virtues, into the hydrogel of the present invention. The Applicant has obtained excellent results using a water-glycerine extract of *calendula officinalis*, at a concentration of 0.2 to 0.5%.

With regard to the cosmetic use of the hydrogel and the dehydration product thereof, but in particular the dermatological use of the said dehydration product, it is desirable to have available sterile samples of hydrogel compatible with a pharmaceutical use. The sterilisation of the hydrogel is preferably effected by autoclaving or by irradiation with sterilising radiation, for example a sufficient dose of gamma radiation.

In a particular embodiment of the present invention, the hydrogel is packed in the form of unit doses with the intention of preventing bacterial contamination due to prolonged storage after opening.

A further subject of the present invention is a process for the preparation of the hydrogel as defined above. This process comprises the following consecutive stages:

Stage 1—preparation of an acidic aqueous solution of a chitosan having a deacetylation level comprised between 85 and 95%, the said solution exhibiting a pH comprised between 4.5 and 5.5 adjusted by the addition of an organic acid of formula R—COOH, where R represents a $C_{1-4}$ alkyl group, preferably a methyl group, Stage 2—reaction of the acid addition salt of chitosan in aqueous solution thus obtained with 0.5 to 1 mole, per mole of D-glucosamine units ((B) units), of an anhydride of an organic diacid of formula HOOC—$(CH_2)_n$—COOH where n represents an integer comprised between 1 and 8, preferably between 1 and 4 and in particular equal to 2, then Stage 3—adjustment of the pH of the reaction solution thus obtained to a value comprised between 6.5 and 7.2 by the addition of a physiologically acceptable base.

The chitosan concentration of the solution from stage 1 is preferably comprised between 5 and 150 g/l, in particular between 10 and 50 g/l. In a preferred embodiment, the appropriate quantity of deacetylated chitosan, in powder form, is suspended in purified water with stirring, and the organic acid is added slowly, preferably in a quantity equimolar to the number of glucosamine units. This stage, preferably carried out at ambient temperature, can take several tens of minutes. A modification of this stage consists in first acidifying the water with the appropriate quantity of acid and then introducing the chitosan.

This stage of dissolution by acidification can be followed or preceded by the addition of a small quantity of hydrogen peroxide, intended, if necessary, to reduce the molecular mass of chitosan by oxidative cleavage of the macromolecular skeleton. The quantity of hydrogen peroxide is preferably comprised between 0.01% and 0.03%.

The reaction of the dicarboxylic acid anhydride is preferably carried out at a temperature comprised between 20° C. and 30° C., with stirring, for a period comprised for example between 45 minutes and 90 minutes. The anhydride can be added in two or more lots and between the different additions the solution can be neutralised by the addition of a base. After the addition and reaction of the whole of the anhydride, the solution is progressively neutralised with a dilute basic solution, for example a dilute solution of soda or potash, taking care not to cause the precipitation of the chitosan by the excessively rapid addition of base. The product thus obtained is a hydrogel according to the invention and need not be subjected to other treatment or concentration stages.

A further subject of the present invention is the utilisation of the hydrogel based on chitosan carboxyalkylamide described above for the cosmetic treatment of first degree burns and of non-weeping, i.e. superficial, second degree burns by application of the said hydrogel onto the burn area. The utilisation of the hydrogel is carried out by simple topical application to the areas affected, one or more times per day, until the problems disappear. This is not a dermatological treatment since on first degree burns or non-weeping second degree burns the hydrogel acts only at the level of the epidermis and does not come into contact with the underlying dermis.

The cosmetic composition containing the hydrogel according to the present invention can further contain other cosmetic active substances or additives such as in particular perfumes, colorants, and texturizing agents.

In the course of its researches aiming to perfect the hydrogel described above, the Applicant found that the hydrogel could be dehydrated by known processes such as lyophilisation, atomisation and spray drying and that the anhydrous product could be used as such, without prior reconstitution by the addition of water, for cosmetic purposes on first degree burns and non-weeping second degree burns, and moreover exhibited the advantage of being very suitable for dermatological utilisation on weeping, i.e. deep, second degree burns and third degree burns.

In fact the dehydration product of the hydrogel, provided that it has a sufficiently fine grain size, spreads easily on the skin, like the hydrogel from which it has been prepared, and there exerts a pain soothing effect and a healing effect. Quite surprisingly, the products of dehydration of the hydrogel according to the present invention thus seem to penetrate into the skin without leaving visible traces.

A further subject of the present invention is thus an anhydrous product based on chitosan carboxyalkylamide obtained by dehydration of the hydrogel described above. The dehydration process can be any known dehydration process, by evaporation of the water from the composition under vacuum and/or with heating. The Applicant has obtained products of excellent quality by lyophilisation and by spray drying or drying by atomisation, and the dehydration process is consequently preferably selected from these last two.

Also a subject of the present invention is the said anhydrous product as a medicament and as a medical device, preferably for topical application and preferably intended for the treatment of deep, weeping second degree burns and third degree burns.

Finally, a subject of the present invention is a cosmetic composition and a dermatological composition containing the anhydrous product described above.

EXAMPLE 1

Process for the Preparation of a Hydrogel of Chitosan Carboxyalkylamide According to the Present Invention 36 litres of purified water are introduced into a vat of 50 litre volume, and 926.6 g of Kitomer chitosan powder (Marinard) having a deacetylation level of 94.4% and a moisture content of 2.87% are slowly poured into this with stirring at 2000 to 3000 revolutions per minute. After stirring for a quarter of an hour, 319 g of acetic acid (about 1 mole equivalent relative to the number of glucosamine units of the chitosan) are added, and the stirring is continued at ambient temperature for a few more minutes. Next, 0.1 g of 30% $H_2O_2$ is added and the mixture is allowed to stand for about 1 hour. Next, with vigorous stirring, about 133 g of succinic anhydride (about 0.30 mole equivalents relative to the number of glucosamine units of the chitosan) are added to the mixture and the stirring is continued for about minutes. The solution obtained is neutralised very gradually by the slow addition of about 160 g of soda diluted in 1.5 litres of water with stirring and over a period of about 15 minutes. The succinic anhydride addition and the neutralisation stage are repeated, taking care that the pH of the solution does not rise beyond the desired final value, comprised between 6.5 and 7.2.

By following the above operating procedure, about 39 litres of gel ready for use or ready to be subjected to a dehydration stage are obtained.

EXAMPLE 2

Process for the Preparation of a Water-Glycerine Gel Containing *Calendula* Extract 1.5 litres of water-glycerine extract of *Calendula officinalis* are mixed with 3.5 litres of glycerol Ph. Eur., then 6 litres of water are added. The solution thus obtained is mixed with the 39 litres of hydrogel prepared in Example 1.

The product thus obtained is then subjected to a dose of 25 kGy of gamma irradiation.

EXAMPLE 3

Treatment of Deep Second Degree Burns with a Dehydration Product Obtained from the Hydrogel A sterile powder obtained by atomisation of a hydrogel prepared according to Example 1, constituted by 10 to 30 µm spherical particles is applied to three deep second degree burns, caused by laser treatment on the back of the hand. The burns have a diameter of about 5 mm. A fourth control burn, identical to the three others, is given no treatment.

The control, untreated burn takes between three and four weeks to heal and disappear.

The three burns treated at the rate of 6 applications on the first day and 2 applications on the following day no longer display any inflammatory symptom after 48 hours and are invisible after four days. The pain disappears after the first application.

FIG. 1 shows a photograph of the back of the hand after 48 hours, with the control burn on the left and the three treated burns on the right.

EXAMPLE 4

Treatment of a First Degree Burn with the Hydrogel

The back of a hand scalded by pouring boiling water (first degree burn) is treated by the application of the hydrogel of Example 1 immediately after the burn (less than 5 minutes afterwards), then after about half an hour and again after 2 hours.

The pain ceases after the first application. The hand remains red for about 6 hours. On the following day, there is no longer any trace of the burn.

The invention claimed is:

1. A hydrogel of chitosan carboxyalkylamide, having a pH value between 6.5 and 7.2, said chitosan carboxyalkylamide being constituted by from 40 to 90 mole %, relative to the total number of (A) and (B) units, of D-glucosamine N-carboxyalkylamide units of formula (I) ((A) units)

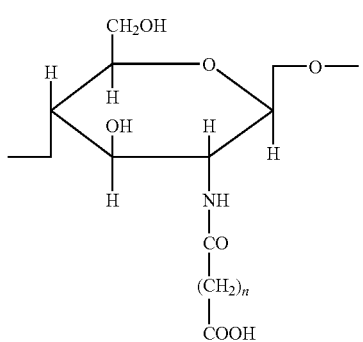

(I)

where n represents an integer ranging from 1 to 8, or a physiologically acceptable base addition salt thereof,
from 60 to 10 mole %, relative to the total number of (A) and (B) units, of protonated D-glucosamine units of formula (II) ((B) units)

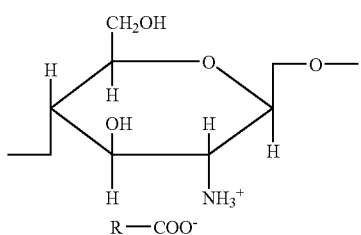

(II)

and 5.5 obtained by the addition of an organic acid of formula R—COOH, where R represents a $C_{1-4}$ alkyl group,
reaction of the acid addition salt of chitosan in aqueous solution thus obtained with 0.5 to 1 mole, per mole of D-glucosamine units ((B) units), of an anhydride of an organic diacid of formula HOOC—$(CH_2)_n$—COOH where n represents an integer comprised between 1 and 8, then
adjustment of the pH of the reaction solution thus obtained to a value between 6.5 and 7.2 by the addition of a physiologically acceptable base.

2. The hydrogel according to claim 1, wherein R represents a methyl group.

3. The hydrogel according to claim 1, having a pH between 6.8 and 7.0.

4. The hydrogel according to claim 1, wherein the concentration of chitosan carboxyalkylamide is between 0.5 and 3% by weight.

5. The hydrogel according to claim 1, which further comprises from 0.1 to 40% by weight, of at least one polyol.

6. The hydrogel according to claim 1, which further comprises a water-glycerine extract of *calendula officinalis*.

7. The hydrogel according to claim 1, wherein said hydrogel is sterile.

8. The hydrogel according to claim 1, which is packed in the form of a unit dose.

9. A process for the preparation of a hydrogel according to claim 1, comprising the following consecutive stages
preparation of an acidic aqueous solution of a chitosan having a deacetylation level between 85 and 95%, the said solution having a pH between 4.5

10. A process of using the hydrogel according to claim 1 for the cosmetic treatment of first degree burns and of non-weeping, superficial second degree burns comprising the application of said hydrogel to the burn area consisting of first degree burns and of non-weeping, superficial second degree burns consisting of first degree burns and of non-weeping, superficial second degree burns.

11. An anhydrous product based on chitosan carboxy-alkylamide obtained by the dehydration of the hydrogel according to claim 1.

12. The anhydrous product according to claim 11, as a medicament intended for the treatment of deep, weeping second degree burns or of third degree burns.

13. The anhydrous product according to claim 11, as a medical device intended for the treatment of deep, weeping second degree burns or of third degree burns.

14. A dermatological composition containing an anhydrous product according to claim 11.

15. A cosmetic composition containing an anhydrous product according to claim 11.
wherein R represents a $C_{1-4}$ alkyl residue, and
from 5 to 15 mole %, relative to the total number of (A), (B) and (C) units, of N-acetyl-D-glucosamine units ((C) units).

16. The hydrogel according to claim 5, wherein the polyol is glycerol.

* * * * *